United States Patent
Sela et al.

(10) Patent No.: US 10,543,045 B2
(45) Date of Patent: Jan. 28, 2020

(54) SYSTEM AND METHOD FOR PROVIDING A CONTOUR VIDEO WITH A 3D SURFACE IN A MEDICAL NAVIGATION SYSTEM

(71) Applicants: Gal Sela, Toronto (CA); Sean Jy-Shyang Chen, Toronto (CA); Siu Wai Jacky Mak, Toronto (CA); Kamyar Abhari, Toronto (CA); Joshua Lee Richmond, Toronto (CA)

(72) Inventors: Gal Sela, Toronto (CA); Sean Jy-Shyang Chen, Toronto (CA); Siu Wai Jacky Mak, Toronto (CA); Kamyar Abhari, Toronto (CA); Joshua Lee Richmond, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 206 days.

(21) Appl. No.: 15/575,552

(22) PCT Filed: Jul. 13, 2015

(86) PCT No.: PCT/CA2015/050651
§ 371 (c)(1),
(2) Date: Nov. 20, 2017

(87) PCT Pub. No.: WO2017/008137
PCT Pub. Date: Jan. 19, 2017

(65) Prior Publication Data
US 2018/0125586 A1  May 10, 2018

(51) Int. Cl.
*A61B 34/20* (2016.01)
*H04N 13/246* (2018.01)
(Continued)

(52) U.S. Cl.
CPC ............ *A61B 34/20* (2016.02); *G06T 19/003* (2013.01); *H04N 13/246* (2018.05);
(Continued)

(58) Field of Classification Search
CPC ........... G06T 2207/10028; G06T 17/00; G06T 19/00; H04N 13/204; H04N 13/246;
(Continued)

(56) References Cited

U.S. PATENT DOCUMENTS 5,151,856 A * 9/1992 Halmann ................ G06T 15/00
600/410
2007/0172101 A1 * 7/2007 Kriveshko ........... A61B 5/4547
382/128
(Continued)

FOREIGN PATENT DOCUMENTS

CN              103267491 A1    8/2013

*Primary Examiner* — Haixia Du
(74) *Attorney, Agent, or Firm* — Rideout & Maybee LLP

(57) ABSTRACT

A medical navigation system for displaying a three dimensional (3D) surface video of a target is provided. The medical navigation system comprises a 3D imaging device, a camera, a display, and a controller electrically coupled to the 3D imaging device, the camera, and the display. The controller has a processor coupled to a memory. The controller is configured to perform calibration of input devices; acquire 3D depth data of the target from a signal generated by the 3D imaging device; construct a 3D surface contour of the target based on the 3D depth data; acquire a video stream of the target from a signal generated by the camera; generate a 3D surface video based on the 3D surface contour and the video stream; and display the 3D surface video on the display.

22 Claims, 10 Drawing Sheets

(51) Int. Cl.
*H04N 13/254* (2018.01)
*G06T 19/00* (2011.01)
*A61B 90/00* (2016.01)
*A61B 90/10* (2016.01)

(52) U.S. Cl.
CPC .... *H04N 13/254* (2018.05); *A61B 2034/2057* (2016.02); *A61B 2090/103* (2016.02); *A61B 2090/363* (2016.02); *A61B 2090/367* (2016.02); *A61B 2090/3735* (2016.02); *G06T 2207/30016* (2013.01); *G06T 2207/30096* (2013.01)

(58) Field of Classification Search
CPC ...... H04N 5/2257; A61B 34/20; A61B 90/37; A61B 5/00
See application file for complete search history.

(56) References Cited

U.S. PATENT DOCUMENTS

| | | | |
|---|---|---|---|
| 2008/0123927 A1* | 5/2008 | Miga | G06T 7/344 382/131 |
| 2009/0012509 A1 | 1/2009 | Csavoy et al. | |
| 2009/0177081 A1 | 7/2009 | Joskowicz et al. | |
| 2010/0238264 A1 | 9/2010 | Liu et al. | |
| 2010/0245549 A1 | 9/2010 | Allen et al. | |
| 2012/0206452 A1* | 8/2012 | Geisner | G02B 27/017 345/419 |
| 2013/0102893 A1 | 4/2013 | Vollmer et al. | |
| 2013/0293690 A1 | 11/2013 | Olson | |
| 2015/0224650 A1* | 8/2015 | Xu | B25J 15/0608 700/213 |

* cited by examiner

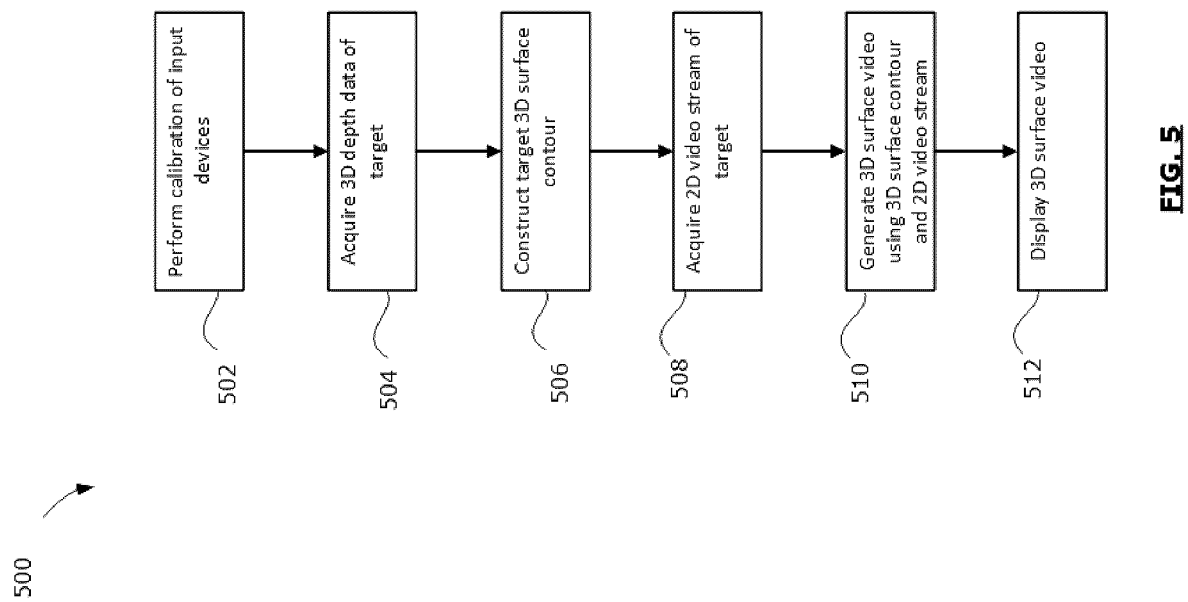

SYSTEM AND METHOD FOR PROVIDING A CONTOUR VIDEO WITH A 3D SURFACE IN A MEDICAL NAVIGATION SYSTEM

TECHNICAL FIELD

The present disclosure is generally related to neurosurgical or medical procedures, and more specifically to a system and method for providing a contour video with a 3D surface in a medical navigation system.

BACKGROUND

In the field of medicine, imaging and image guidance are a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy. Targeted stem cell delivery, adaptive chemotherapy regimes, and radiation therapy are only a few examples of procedures utilizing imaging guidance in the medical field.

Advanced imaging modalities such as Magnetic Resonance Imaging ("MRI") have led to improved rates and accuracy of detection, diagnosis and staging in several fields of medicine including neurology, where imaging of diseases such as brain cancer, stroke, Intra-Cerebral Hemorrhage ("ICH"), and neurodegenerative diseases, such as Parkinson's and Alzheimer's, are performed. As an imaging modality, MRI enables three-dimensional visualization of tissue with high contrast in soft tissue without the use of ionizing radiation. This modality is often used in conjunction with other modalities such as Ultrasound ("US"), Positron Emission Tomography ("PET") and Computed X-ray Tomography ("CT"), by examining the same tissue using the different physical principals available with each modality. CT is often used to visualize boney structures and blood vessels when used in conjunction with an intra-venous agent such as an iodinated contrast agent. MRI may also be performed using a similar contrast agent, such as an intra-venous gadolinium based contrast agent which has pharmaco-kinetic properties that enable visualization of tumors and break-down of the blood brain barrier. These multi-modality solutions can provide varying degrees of contrast between different tissue types, tissue function, and disease states. Imaging modalities can be used in isolation, or in combination to better differentiate and diagnose disease.

In neurosurgery, for example, brain tumors are typically excised through an open craniotomy approach guided by imaging. The data collected in these solutions typically consists of CT scans with an associated contrast agent, such as iodinated contrast agent, as well as MRI scans with an associated contrast agent, such as gadolinium contrast agent. Also, optical imaging is often used in the form of a microscope to differentiate the boundaries of the tumor from healthy tissue, known as the peripheral zone. Tracking of instruments relative to the patient and the associated imaging data is also often achieved by way of external hardware systems such as mechanical arms, or radiofrequency or optical tracking devices. As a set, these devices are commonly referred to as surgical navigation systems.

Three dimensional (3D) sensor systems are increasingly being used in a wide array of applications, including medical procedures. These sensor systems determine the shape and/or features of an object positioned in a scene of the sensor system's view. In recent years, many methods have been proposed for implementing 3D modeling systems that are capable of acquiring fast and accurate high resolution 3D images of objects for various applications.

Triangulation based 3D sensor systems and methods typically have one or more projectors as a light source for projecting onto a surface and one or more cameras at a defined, typically rectified relative position from the projector for imaging the lighted surface. The camera and the projector therefore have different optical paths, and the distance between them is referred to as the baseline. Through knowledge of the baseline distance as well as projection and imaging angles, known geometric/triangulation equations are utilized to determine distance to the imaged object. The main differences among the various triangulation methods known in the art lie in the method of projection as well as the type of light projected, typically structured light, and in the process of image decoding to obtain three dimensional data.

A 3D sensor system may be contemplated as a novel extension of a surgical navigation system. One popular triangulation based 3D sensor system is created by Mantis Vision, which utilizes a single frame structured light active triangulation system to project infrared light patterns onto an environment. To capture 3D information, a projector overlays an infrared light pattern onto the scanning target. Then a digital camera and a depth sensor, synched to the projector, captures the scene with the light reflected by the object. The technology works even in complete darkness, since it includes its own illumination; in bright environments the quality of the resulting image depends on the hardware used.

Video streams, such as from an exoscope, do not provide 3D depth information. Conventional stereo solutions require multiple camera sensors, one for each eye. This approach has a number of limitations, including cost since twice the optical hardware is needed, difficulty in applying such solutions down a restricted aperture such as the port because of physical size, only being visualized with a stereo display such as goggles, and a failure to provide any absolute depth measurement information.

Therefore, there is a need for an improved system and method for providing 3D visualization of patient tissue during a medical procedure.

SUMMARY

One aspect of the present disclosure provides a medical navigation system for displaying a three dimensional (3D) surface video of a target. The medical navigation system comprises a 3D imaging device, a camera, a display, and a controller electrically coupled to the 3D imaging device, the camera, and the display. The controller has a processor coupled to a memory. The controller is configured to perform calibration of input devices; acquire 3D depth data of the target from a signal generated by the 3D imaging device; construct a 3D surface contour of the target based on the 3D depth data; acquire a video stream of the target from a signal generated by the camera; generate a 3D surface video based on the 3D surface contour and the video stream; and display the 3D surface video on the display.

Another aspect of the present disclosure provides a method for displaying a three dimensional (3D) surface video of a target in a system having a 3D imaging device, a camera, a display, and a controller electrically coupled to the 3D imaging device, the camera, and the display. The method comprises performing calibration of input devices; acquiring 3D depth data of the target from a signal generated by the 3D imaging device; constructing a 3D surface contour of the target based on the 3D depth data; acquiring a video stream of the target from a signal generated by the camera; generating a 3D surface video based on the 3D surface contour and the video stream; and displaying the 3D surface video on the display.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 5 illustrates a flow chart showing a method for displaying a three dimensional surface video of a target;

DETAILED DESCRIPTION

Figure 1:
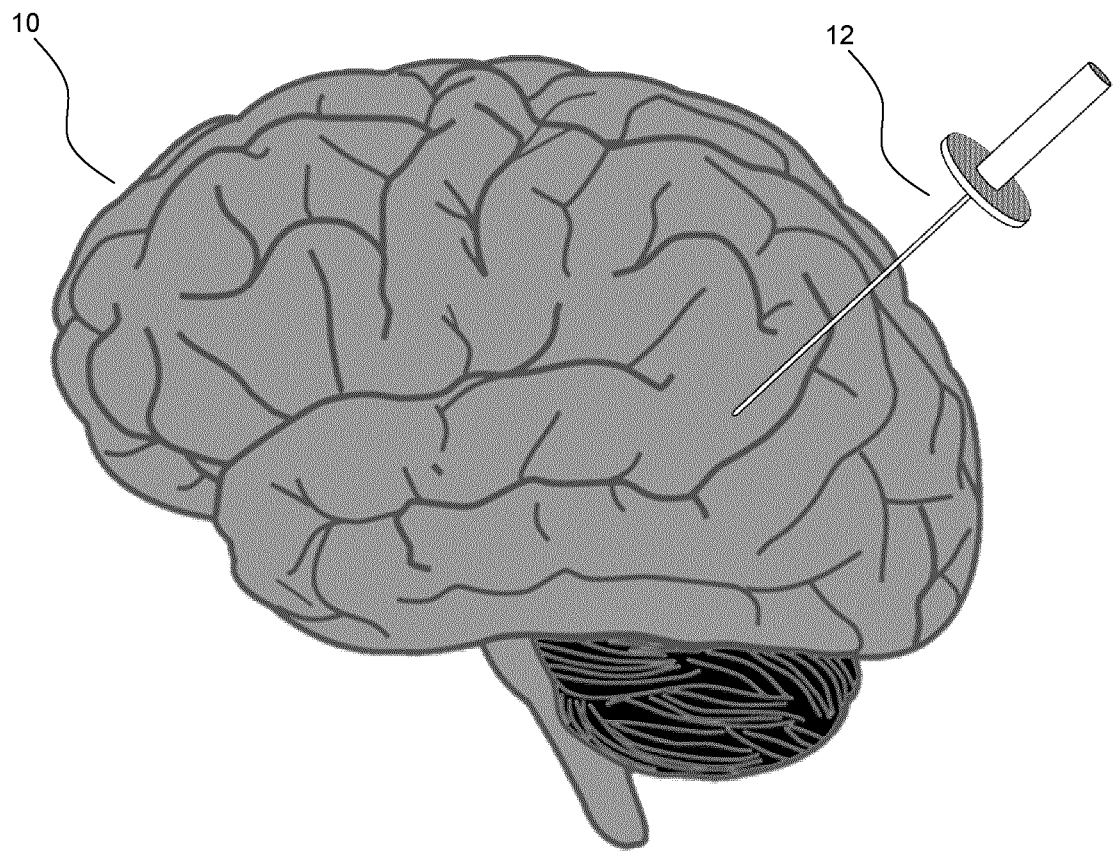
FIG. 1 illustrates the insertion of an access port into a human brain, for providing access to internal brain tissue during a medical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Embodiments of the present disclosure provide imaging devices that are insertable into a subject or patient for imaging internal tissues, and methods of use thereof. Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port.

The present disclosure is generally related to medical procedures, neurosurgery, and minimally invasive port-based surgery in specific.

In the example of a port-based surgery, a surgeon or robotic surgical system may perform a surgical procedure involving tumor resection in which the residual tumor remaining after is minimized, while also minimizing the trauma to the healthy white and grey matter of the brain. In such procedures, trauma may occur, for example, due to contact with the access port, stress to the brain matter, unintentional impact with surgical devices, and/or accidental resection of healthy tissue. A key to minimizing trauma is ensuring that the spatial location of the patient as understood by the surgeon and the surgical system is as accurate as possible.

One aspect of the present disclosure provides combining surface contour information with a video stream allowing the video image to be perceived in 3D. This enables a number of display options, including: (a) contour topography can be tipped obliquely giving 3D surface information of the video without need for goggles to view; (b) contour topography can be tipped and rotated dynamically showing the video projected onto the surfaces from any view angle; specific depth measurements (e.g., in millimeters) can be assessed and displayed; and when viewed with 3D goggles the display may show the 3D video with each point at a specified depth.

FIG. 1 illustrates the insertion of an access port into a human brain, for providing access to internal brain tissue during a medical procedure. In FIG. 1, access port 12 is inserted into a human brain 10, providing access to internal brain tissue. Access port 12 may include instruments such as catheters, surgical probes, or cylindrical ports such as the NICO BrainPath. Surgical tools and instruments may then be inserted within the lumen of the access port in order to perform surgical, diagnostic or therapeutic procedures, such as resecting tumors as necessary. The present disclosure applies equally well to catheters, DBS needles, a biopsy procedure, and also to biopsies and/or catheters in other medical procedures performed on other parts of the body where head immobilization is needed.

In the example of a port-based surgery, a straight or linear access port 12 is typically guided down a sulci path of the brain. Surgical instruments would then be inserted down the access port 12.

Optical tracking systems, which may be used in the medical procedure, track the position of a part of the instrument that is within line-of-site of the optical tracking camera. These optical tracking systems also require a reference to the patient to know where the instrument is relative to the target (e.g., a tumor) of the medical procedure. These optical tracking systems require a knowledge of the dimensions of the instrument being tracked so that, for example, the optical tracking system knows the position in space of a tip of a medical instrument relative to the tracking markers being tracked.

Figure 2:
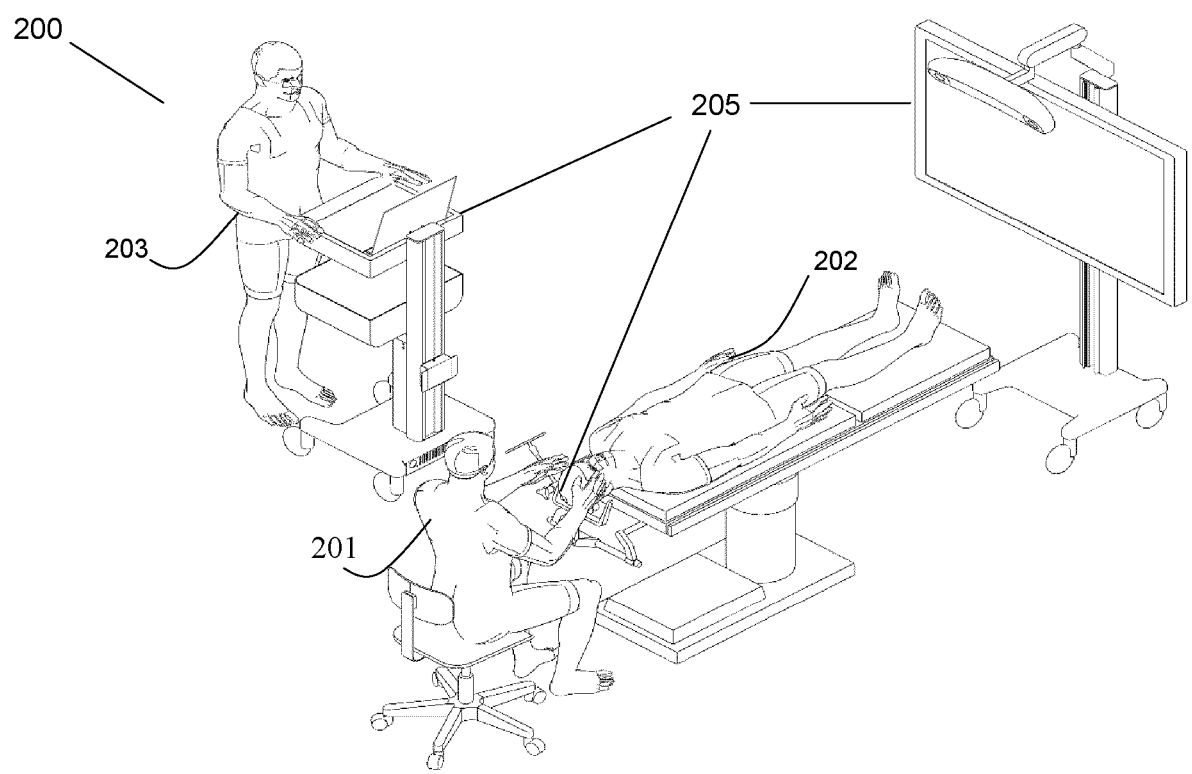
FIG. 2 shows an exemplary navigation system to support minimally invasive access port-based surgery.

Referring to FIG. 2, an exemplary navigation system environment 200 is shown, which may be used to support navigated image-guided surgery. As shown in FIG. 2, surgeon 201 conducts a surgery on a patient 202 in an operating room (OR) environment. A medical navigation system 205 comprising an equipment tower, tracking system, displays and tracked instruments assist the surgeon 201 during his procedure. An operator 203 is also present to operate, control and provide assistance for the medical navigation system 205.

Figure 3:
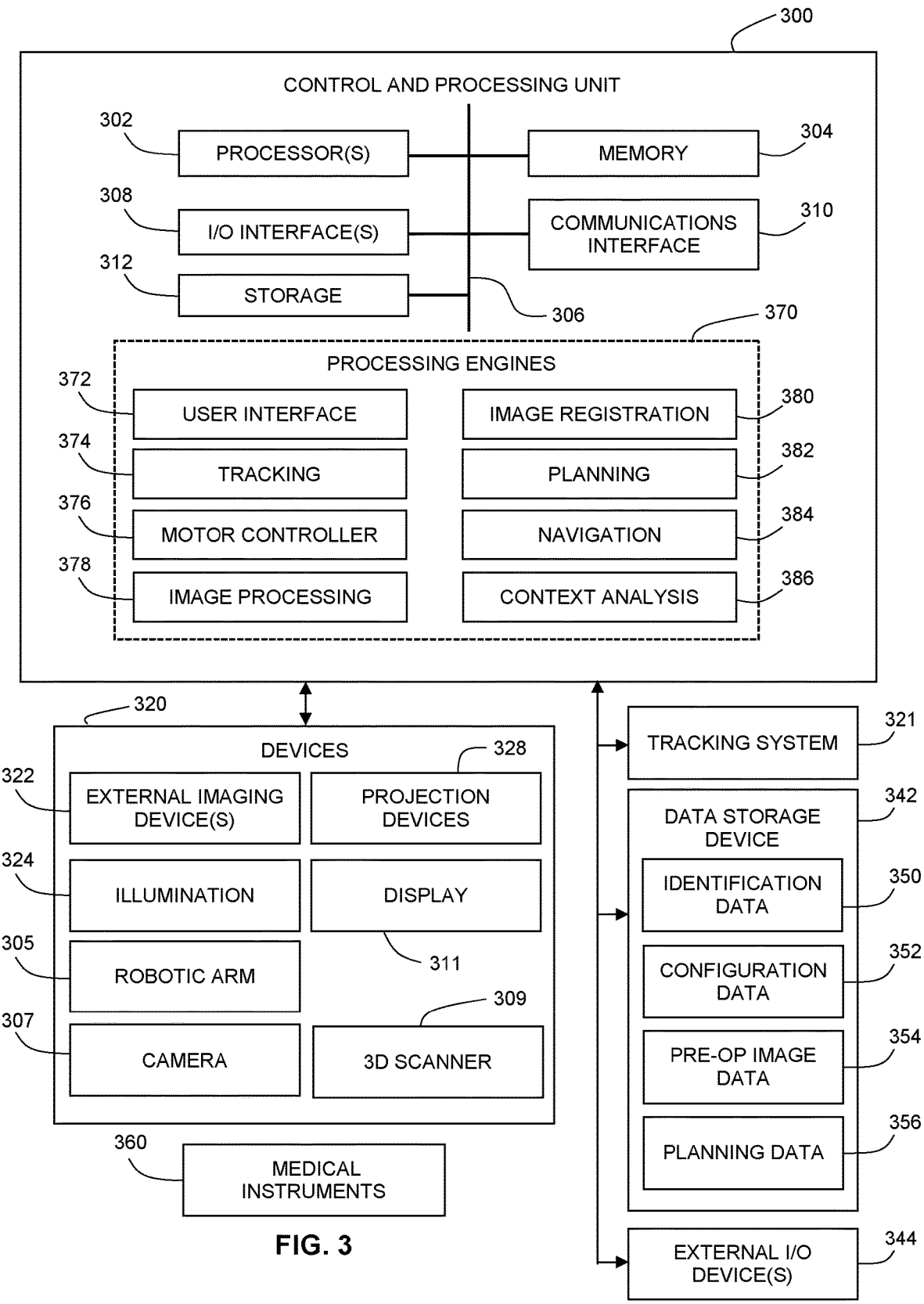
FIG. 3 is a block diagram illustrating a control and processing system that may be used in the navigation system shown in FIG. 2.

Referring to FIG. 3, a block diagram is shown illustrating a control and processing system 300 that may be used in the medical navigation system 205 shown in FIG. 2 (e.g., as part of the equipment tower). As shown in FIG. 3, in one example, control and processing system 300 may include one or more processors 302, a memory 304, a system bus 306, one or more input/output interfaces 308, a communications interface 310, and storage device 312. Control and processing system 300 may be interfaced with other external devices, such as tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 3, data storage device 342 includes identification data 350 for identifying one or more medical instruments 360 and configuration data 352 that associates customized configuration parameters with one or more medical instruments 360. Data storage device 342 may also include preoperative image data 354 and/or medical procedure planning data 356. Although data storage device 342 is shown as a single device in FIG. 3, it will be understood that in other embodiments, data storage device 342 may be provided as multiple storage devices.

Medical instruments 360 are identifiable by control and processing unit 300. Medical instruments 360 may be connected to and controlled by control and processing unit 300, or medical instruments 360 may be operated or otherwise employed independent of control and processing unit 300. Tracking system 321 may be employed to track one or more of medical instruments 360 and spatially register the one or more tracked medical instruments to an intraoperative reference frame. For example, medical instruments 360 may include tracking markers such as tracking spheres that may be recognizable by a tracking camera 307. In one example, the tracking camera 307 may be an infrared (IR) tracking camera. In another example, as sheath placed over a medical instrument 360 may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include one or more external imaging devices 322, one or more illumination devices 324, a robotic arm 305, one or more projection devices 328, a 3D scanner 309, and one or more displays 311.

Exemplary aspects of the disclosure can be implemented via processor(s) 302 and/or memory 304. For example, the functionalities described herein can be partially implemented via hardware logic in processor 302 and partially using the instructions stored in memory 304, as one or more processing modules or engines 370. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example the processing modules 370 may be stored in the memory 304 and the processing modules may be collectively referred to as processing modules 370.

It is to be understood that the system is not intended to be limited to the components shown in FIG. 3. One or more components of the control and processing system 300 may be provided as an external component or device. In one example, navigation module 384 may be provided as an external navigation system that is integrated with control and processing system 300.

Some embodiments may be implemented using processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

According to one aspect of the present application, one purpose of the navigation system 205, which may include control and processing unit 300, is to provide tools to the neurosurgeon that will lead to the most informed, least damaging neurosurgical operations. In addition to removal of brain tumors and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to any suitable medical procedure.

While one example of a navigation system 205 is provided that may be used with aspects of the present application, any suitable navigation system may be used, such as a navigation system using optical tracking instead of infrared cameras.

Figure 4A:
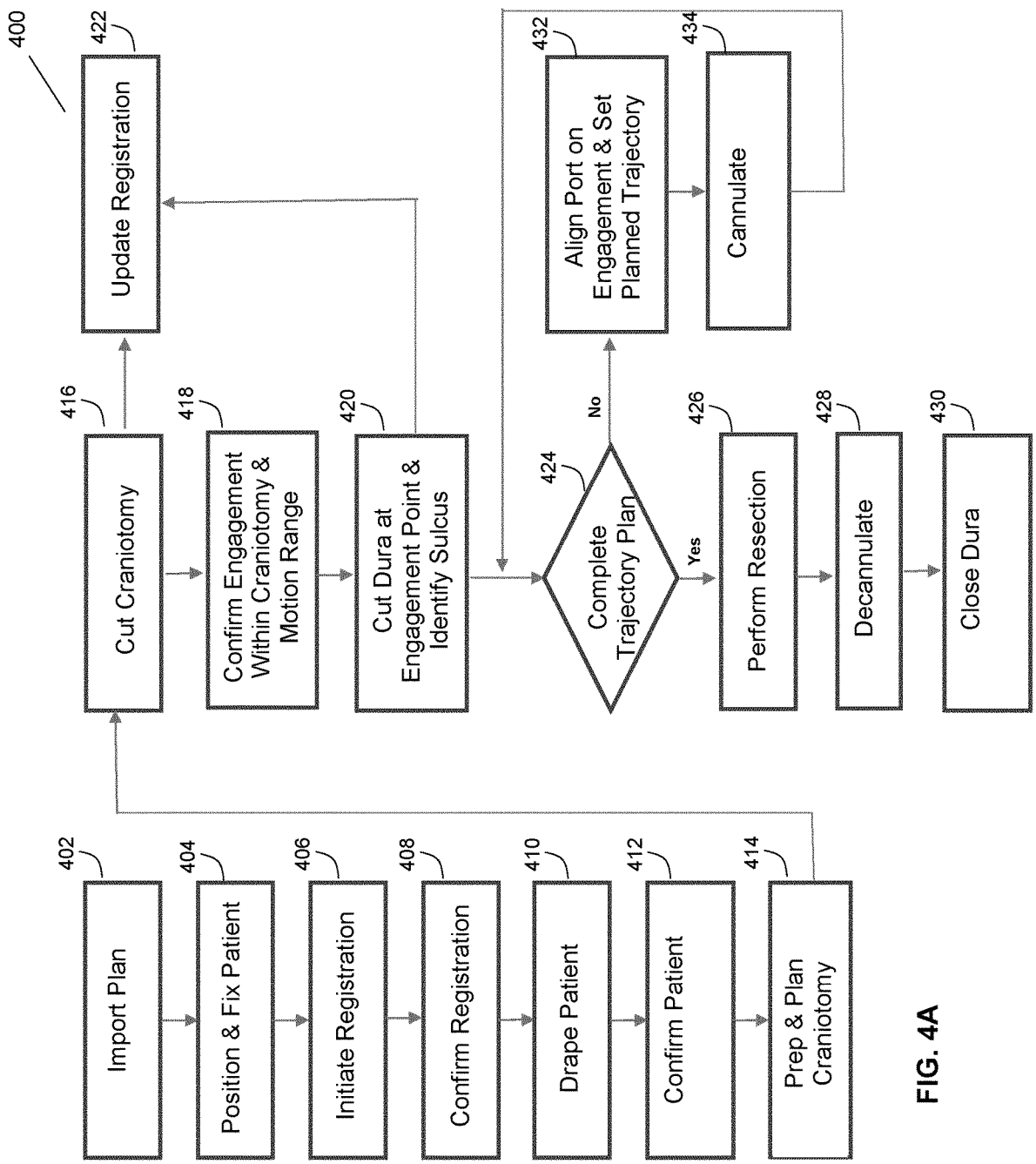
FIG. 4A is a flow chart illustrating a method involved in a surgical procedure using the navigation system of FIG. 2.

Referring to FIG. 4A, a flow chart is shown illustrating a method 400 of performing a port-based surgical procedure using a navigation system, such as the medical navigation system 205 described in relation to FIG. 2. At a first block 402, the port-based surgical plan is imported. A detailed description of the process to create and select a surgical plan is outlined in international publication WO/2014/139024, entitled "PLANNING, NAVIGATION AND SIMULATION SYSTEMS AND METHODS FOR MINIMALLY INVASIVE THERAPY", which claims priority to U.S. Provisional Patent Application Ser. Nos. 61/800,155 and 61/924,993, which are all hereby incorporated by reference in their entirety.

Once the plan has been imported into the navigation system at the block 402, the patient is placed on a surgical bed. The head position is confirmed with the patient plan in the navigation system (block 404), which in one example may be implemented by a computer or controller forming part of the equipment tower.

Next, registration of the patient is initiated (block 406). The phrase "registration" or "image registration" refers to the process of transforming different sets of data into one coordinate system. Data may include multiple photographs, data from different sensors, times, depths, or viewpoints. The process of "registration" is used in the present application for medical imaging in which images from different imaging modalities are co-registered. Registration is used in order to be able to compare or integrate the data obtained from these different modalities to the patient in physical space.

Those skilled in the relevant arts will appreciate that there are numerous registration techniques available and one or more of the techniques may be applied to the present example. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in magnetic resonance imaging (MRI) and positron emission tomography (PET). In the present disclosure, multi-modality registration methods may be used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT to patient in physical space.

Figure 4B:
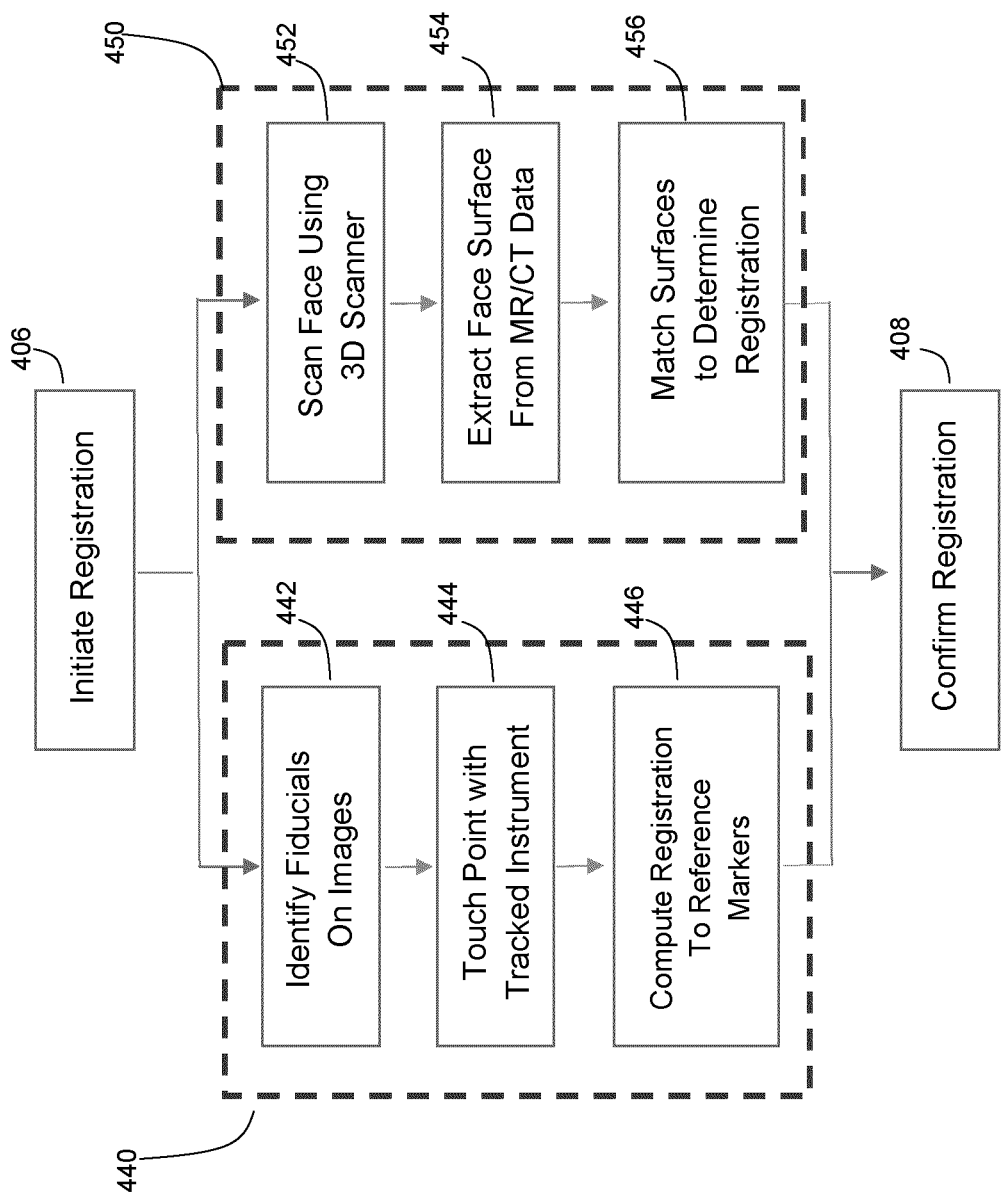
FIG. 4B is a flow chart illustrating a method of registering a patient for a surgical procedure as outlined in FIG. 4A.

Referring now to FIG. 4B, a flow chart is shown illustrating a method involved in registration block 406 as outlined in FIG. 4A, in greater detail. If the use of fiducial touch points (440) is contemplated, the method involves first identifying fiducials on images (block 442), then touching the touch points with a tracked instrument (block 444). Next, the navigation system computes the registration to reference markers (block 446).

Alternately, registration can also be completed by conducting a surface scan procedure (block 450), which may be applied to aspects of the present disclosure. The block 450 is presented to show an alternative approach. First, the face is scanned using a 3D scanner (block 452). Next, the face surface is extracted from MR/CT data (block 454). Finally, surfaces are matched to determine registration data points (block 456).

Upon completion of either the fiducial touch points (440) or surface scan (450) procedures, the data extracted is computed and used to confirm registration at block 408, shown in FIG. 4A.

Referring back to FIG. 4A, once registration is confirmed (block 408), the patient is draped (block 410). Typically, draping involves covering the patient and surrounding areas with a sterile barrier to create and maintain a sterile field during the surgical procedure. The purpose of draping is to eliminate the passage of microorganisms (e.g., bacteria) between non-sterile and sterile areas. At this point, conventional navigation systems require that the non-sterile patient reference is replaced with a sterile patient reference of identical geometry location and orientation. Numerous mechanical methods may be used to minimize the displacement of the new sterile patient reference relative to the non-sterile one that was used for registration but it is inevitable that some error will exist. This error directly translates into registration error between the surgical field and pre-surgical images. In fact, the further away points of interest are from the patient reference, the worse the error will be.

Upon completion of draping (block 410), the patient engagement points are confirmed (block 412) and then the craniotomy is prepared and planned (block 414).

Upon completion of the preparation and planning of the craniotomy (block 414), the craniotomy is cut and a bone flap is temporarily removed from the skull to access the brain (block 416). Registration data is updated with the navigation system at this point (block 422).

Next, the engagement within craniotomy and the motion range are confirmed (block 418). Next, the procedure advances to cutting the dura at the engagement points and identifying the sulcus (block 420).

Thereafter, the cannulation process is initiated (block 424). Cannulation involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424).

Once cannulation is complete, the surgeon then performs resection (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of FIG. 4A are specific to port-based surgery, such as portions of blocks 428, 420, and 434, but the appropriate portions of these blocks may be skipped or suitably modified when performing non-port based surgery.

With a video camera input, such as from a video camera 307, which in one example may be an exoscope, and a calibrated point cloud or 3D surface contour generated using a 3D scanner, such as 3D scanner 309, depth information for each pixel in the camera image can be obtained. This representation can be viewed directly as a 3D point cloud, with each point's colour determined by the matched video image colour. Further, the point cloud may be used to generate a continuous surface representation and the video image may be mapped onto this surface through methods that are known in computer graphics, such as texture mapping. Either of these representations may be used, as discussed in more detail below, and are generally referred to as a 3D surface image or 3D surface video. Further, the image input may be a continuous video stream and the point cloud or surface representation may update continuously to provide a live streaming 3D surface video stream. Finally, the point cloud may be an accumulation of data from multiple 3D distance sensors at multiple viewing angles, providing more detailed depth information, such as filling in detail for surface areas that are occluded to one sensor.

Depth information can be directly visualized from the generated 3D surface images or video streams. This can be achieved in a number of ways. In one example, the contour topography can be tipped obliquely to the user's view position, giving 3D surface information of the image. The view can also be dynamically rotated about any axes, allowing the data to be viewed from all angles, giving a sense of the 3D geometry of the image or video stream data.

Further, since the 3D scanner or imaging device provides measurable depth information at each point, the generated live 3D surface image or video stream can also provide directly measurable depth information to the traditionally flat image or video representations. Direct or relative depth measurements can be made from the surface or point cloud data, allowing, for example, a display of the Euclidean distance including depth between any 2 points in the image data. In a further example, when combined with a medical navigation system, such as the medical navigation system 205 that may have a registered optical or electromagnetic tracking system, a display of the distance from the tip of a tracked surgical instrument, along the tool normal direction, to the surface image data may be provided. Alternatively, a distance from the instrument tip along a transverse direction can display the lateral distance of the tool relative to the surface, which can be, for example, the side of a body cavity or retraction device.

Finally, any of these representations can also be viewed with a stereo display system, such as active or passive stereo 3D glasses, to allow for a true 3D perception of the surface image or video stream. A stereo display is made possible without the need for 2 image acquisition devices, which reduces cost and bulk of the system. Further, in cases where the line of site is limited, such as through a surgical port or through an endoscope, it may not be possible to get a good view of the surface with stereo imaging sensors separated by sufficient distance to provide proper stereo perception.

Referring now to FIG. 5, a flow chart is shown illustrating a method 500 for displaying a three dimensional (3D) surface video of a target. The method 500 may be applied in a system, such as the medical navigation system 205 having control and processing unit 300, which includes a 3D imaging device (e.g., 3D scanner 309), a video camera (e.g., camera 307), a display (e.g., display 311), and a controller (e.g., the processor 302) electrically coupled to the 3D imaging device, the video camera, and the display. While a video camera is used as an example, any suitable type of camera may be used such as a video camera, an infrared camera, a visible light camera, or a non-visible light camera.

At a first block 502, calibration of input devices is performed. The video camera 307 and the 3D scanner 309 may be configured to remain in a known, calibrated position relative to one another. In some embodiments, calibration may also involve the tracking system 321. In one example, the calibration of the 3D scanner 309 with the video camera 307 may be done before the method 500 is executed or at the beginning of the method 500 since the spatial relation of the 3D scanner 309 with the video camera 307 needs to be known before a 3D surface video can be created. In one example, the video camera may be an RGB video camera.

In one example, calibration may be used to accurately map information from one coordinate system to another. In method 500, the spatial relationship between the 3D scanner 309, video camera 307, and optionally, the tracking system 321 may be determined through a multistep calibration process including: (1) depth calibration, (2) video camera calibration, (3) IR (e.g., infrared tracking system) to video camera calibration, (4) IR to optical camera calibration, where an optical tracking system is used, and (5) multiple IR camera registration and synchronization. These processes may carried out a single time prior to or at the beginning of the method 500. These components of the calibration process are described in more detail below.

Depth calibration: Depth calibration involves determining the correspondence between features of a particular pattern projected by a laser emitter of the 3D scanner 309 (e.g., that appear along pre-determined epipolar lines) and the points in space from which the features are reflected. For more information, refer to Golrdon, Eyal, and Gur Arie Bittan. "3D geometric modeling and motion capture using both single and dual imaging." U.S. Pat. No. 8,090,194. 3 Jan. 2012, the entirety of which is hereby incorporated by reference.

Video camera and IR camera (e.g., infrared tracking system) calibration: This step involves performing camera resectioning, often called camera calibration, for both the IR camera and the video camera to identify the camera intrinsic and extrinsic parameters (respectively, focal lengths/principal points ($f_x$, $f_y$, $c_x$, $c_y$) and [R T]) as well as lens distortion coefficients ($k_1$, $k_2$, $k_3$, $p_1$, $p_2$). There are many different approaches to camera resectioning including, but not limited to, direct linear transformation (DLT), Tsai's method, as detailed in Tsai, Roger Y. "A versatile camera calibration technique for high-accuracy 3D machine vision metrology using off-the-shelf TV cameras and lenses." Robotics and Automation, IEEE Journal of 3.4 (1987): 323-344, the entirety of which is hereby incorporated by reference, and Zhang's method, detailed by Zhang, Zhengyou. "A flexible new technique for camera calibration." Pattern Analysis and Machine Intelligence, IEEE Transactions on 22.11 (2000): 1330-1334, the entirety of which is hereby incorporated by reference.

Video camera (e.g., an RGB camera) to IR camera calibration: Calibrating the video camera to IR camera can be achieved via either of the following methods: (a) if both the video camera and the IR camera are tracked by an optical tracker (e.g., a set of reference markers known as dynamic reference body (DRB) are attached to their rigid bodies), the relationship between two cameras can be easily computed:

$$^{RGB}T_{IR} = {}^{optical\ tracker}T_{RGB}^{-1} \times {}^{optical\ tracker}T_{IR}$$

Assuming that both the video camera and the IR camera (e.g., infrared tracking system) can be approximated by the pinhole camera model and that their relative geometry does not vary through the course of procedure, the spatial relationship between the video camera and the IR camera coordinate systems can be determined from the projections of corresponding points in the two cameras. This process is similar to stereo camera calibration explained extensively in the literature Faugeras, Olivier D. "What can be seen in three dimensions with an uncalibrated stereo rig?." Computer Vision-ECCV'92. Springer Berlin Heidelberg, 1992, the entirety of which is hereby incorporated by reference.

3D scanner 309 IR camera to optical tracking camera calibration may be completed as described in PCT Patent Application No. PCT/CA2015/050573, which is hereby incorporated by reference in its entirety.

Multiple IR camera registration and synchronization: The 3D point clouds obtained by two or more IR cameras (e.g., where the 3D imaging device or scanner uses IR technology) can be registered together using a number of 3D-to-3D registration techniques such as an iterative closest point (ICP) algorithm. To this end, scanners are temporally synchronized, circumventing an overlap between multiple patterns. Synchronization may be done by simply sharing the timestamp through a wireless communication between cameras.

In one example, performing the calibration of the input devices at the block 502 includes mapping coordinates of the 3D imaging device, the video camera, and a tracking system of the medical navigation system into a common coordinate system and may include any of the aspects described above, but not necessarily all of them.

Once calibration has been completed, the method 500 proceeds to a block 504 where 3D depth data of the target is acquired from a signal generated by the 3D imaging device. The target may include human tissue, such as a portion of a human that is the subject of a medical procedure, for example brain tissue. The 3D imaging device may be any of a 3D surface scanner, a structured light scanner, an optical coherence tomography (OCT) scanner, a rangefinder, and a focused light beam, or any other suitable 3D imaging device. In the example of a 3D surface scanner, the 3D depth data may be acquired by a user or technician performing a scan of the surface of the target. Alternatively, the medical navigation system 205 may have an automated arm (e.g., robotic arm 3050 that automatically performs the scan.

3D surface scanners, or 3D Scanners, are a class of optical imaging devices that are capable of collecting depth or distance information of objects in its scanning range such that the scanned object's 3D coordinate data can be acquired. These scanners operate through a wide variety of technologies and methods that recover the distance information from scanned objects though analysis of their acquired images. This includes, but is not limited to passive sensor technologies that work by photogrammic analysis of features in the images, or active sensor technologies that may operate through projection and analysis of light with known properties (e.g., by illuminating an object with laser light for point-based triangulation and holographic reconstruction, or through projection of structured light for analysis of pattern deformations).

Of the aforementioned technologies used in hand-held 3D scanners, structured light scanners are among the most common type. Structured light scanning technology uses a projector to project light of a known structure, or pattern, onto objects of interest, such as the target of concern in the present description. The patterned light can be projected using either incoherent or coherent light emitters, depending on the design criteria of a particular application. One or more cameras would then be used to acquire images of the objects illuminated by the projected light, and the distorted pattern from these images is analyzed to reconstruct the 3D surface contour. In the present description, the 3D scanner 309 includes both the projector and the one or more cameras.

The projected structured light can vary from simple geometric forms to more complex 2D coded patterns that may or may not vary spatially or temporally. These patterns may be designed with codified features to disambiguate their locations and to improve scanning accuracy. The types of electromagnetic radiation used for structured light scanning can also range from visible to infra-red light or a mix thereof.

There are several methods of detecting surface contours of tissues. These methods are described as examples only and are not meant to limit the scope of the application.

Optical Coherence Tomography (OCT) is an optical imaging technique that enables visualization of tissue in one, two or three dimensions through the use of optical interferometry. OCT is an optical analog of ultrasound imaging in that it measures the amplitude of the backscattered light (e.g., echoes) returning from a tissue sample as a function of delay. Through scanning the probe beam across the tissue surface and detecting the corresponding echoes from each tissue location, a multi-dimensional image of the tissue structure may be obtained. By extracting the top layer of the tissue in an OCT image through image segmentation, a surface contour of tissue may be obtained. In general, OCT can provide surface contour of an area of a few centimeters by a few centimeters with sub-millimeter resolution.

OCT described here includes, but is not limited to, time domain OCT, frequency domain OCT, spectral domain OCT, swept source OCT, common path OCT, polarization sensitive OCT and full field OCT. In addition, OCT described here includes, but is not limited to, free space based OCT systems, fiber optic based OCT systems and any combination of the two (e.g., free space or fiber hybrid optical systems). The probe beam could be scanned by using, but not limited to, galvanometer or MEMS mirrors.

In another example, tissue contour may be obtained using one or more rangefinders. Rangefinders use electromagnetic waves (e.g., light) pulses to determine the distance of the tissue through time-of-flight techniques. Time-of-flight techniques measure the time taken by the pulse to be reflected off the tissue and return to the sender. By using the propagation speed of the pulse and the measured time, distance of the tissue at the location where the light pulse hits may be calculated. By scanning or projecting light pulses across the tissue surface, a surface contour may be obtained through mapping the calculated distance information spatially.

Instead of using a time-of-flight technique, tissue distance may also be obtained using one or more focused light beams. A focused light beam uses a minimum spot size that is at a fixed distance away from the light source and the lens that focused the beam. Through moving the light source and the lens closer or further away from the tissue while fixing the distance between the light source and the lens, the minimum beam spot may be observed from the tissue. By mapping the positions of the light sources or lens at which the minimum beam spot is observed from each location of the tissue, a surface contour of the tissue may be obtained. Scanning of the light source across of the tissue may be achieved using galvanometers or MEMS mirrors. Multiple light sources and lenses may also be used including but not limiting to the use of microlens array for simultaneous measurement of an area of tissue. An electronically tunable lens could also be used to speed up measurement time.

Once block 504 has been completed, the method 500 proceeds to a block 506 where a 3D surface contour of the target is constructed based on the 3D depth data. In one example, constructing a 3D surface contour includes generating a 3D point cloud of the target based on the 3D depth data. In the example where a structured light 3D scanner is used, the reconstruction of the object's 3D surface contour from a structured light scan may be a multistep process. The desired pattern of the structured light is first projected onto the objects of interest, such as the target. Images of the structured light illuminated objects are acquired by a camera (e.g. at the block 504), and known features contained in the patterned light are extracted. The extracted pattern features from the camera image are then matched to their homologs in the projected image. By measuring the changes in position of the features and accounting for the model parameters of both the camera and the projector with their epipolar geometry, the 3D coordinates on the surface of the objects can be computed (e.g., at the block 506). Adding additional cameras in this process can help improve accuracy of the recovered 3D coordinates. At the block 506, using the 3D coordinates recovered from the scanning the object, the target's surface contour may be reconstructed through a wide variety of methods including those based on point triangulation or globally and locally defined surface fitting methods.

Figure 6:
FIG. 6 is a drawing illustrating an exemplary 3D surface contour of a target.

Referring to FIG. 6, a diagram is shown illustrating an exemplary surface contour 600 including a target 602 showing the surface contour of the target 602. In one example, the target 602 may be human tissue. In one example, the surface contour 600 may be illustrated as a black and white or grayscale collection of points or point cloud. However, the points in the point cloud 600 may also be coloured, according to the design criteria of a particular application.

Returning back to FIG. 5, once block 506 has been completed and the surface contour 600 has been constructed, the method 500 proceeds to a block 508 where a 2D video stream of the target is acquired, for example using the video camera 307.

Next, the method 500 proceeds to a block 510 where a 3D surface video is generated using the 3D surface contour constructed at the block 506 and the 2D video stream acquired at the block 508. The generated 3D surface video is then displayed at the block 512, for example on the display 311. In one example, generating the 3D surface video includes colouring each point of the 3D surface contour or point cloud using colour provided by the video stream.

In one example, the 3D surface video displayed on the display shows a 3D video that is dynamically rotatable about any axis. The display 307 may include a two dimensional video display, a stereo display system, stereo goggles, or any other suitable display for showing a 3D image or video.

The present system and method may perceive and combine certain visual cues to have an overall estimate of depth. Among them, occlusion, or partial blockage of one object's view by another object, is one of the strongest cue in perceiving the relative proximity between objects. In natural images, these cues are compatible, and therefore any conflicting information may cause visual fatigue and degrade the perception. This phenomenon, known as depth misperception, can dramatically affect the outcome of augmented-reality (AR), and particularly surgical AR environments. In such environments, if not handled properly, the occlusion of an operators' hands or medical devices by virtual images can result in conflicting depth cues with incorrect visualization of the medical images. Occlusion handling is a method by which the method 500 may detect and therefore resolve such incompatibility between real and virtual information in AR environments.

A number of conventional solutions have been proposed to handle occlusion in medical AR environments. For instance, hue-based thresholding can be employed to locate and thus mask the surgical gloves worn by the medical practitioner. This technique can be even further optimized by making use of tracking information, whether optical, magnetic, or marker-based, to track surgical tools and thereby optimize the detection process. Another approach is to use visual information such as real-time video captured from two or even multiple cameras and apply techniques such as visual hull or graph-cut to distinguish the foreground from the background, creating different levels of depth (e.g., a depth map). In one example, the method 500 may involve generating the depth map using the data provided by 3D scanner 309. Assuming that the 3D scanner and the tracking system are in the same coordinate space (e.g., registered), having the depth map will provide enough information regarding the location of objects in the 3D space. Therefore, occlusion can be handled by masking out the virtual information at the locations where real objects are detected in between the camera and the surgical site, onto which the virtual images are superimposed.

In one example, occlusion events may be excluded using the 3D surface contour such that an object passing between the target and at least one of the 3D imaging device 309 and the video camera 307 is not visible in the 3D surface video. In one example, this may be achieved such that objects having a depth that is a beyond a threshold distance outside of the 3D surface contour are not shown in the 3D surface video.

Figure 8:
FIG. 8 is screen shot illustrating occlusion handling.
Figure 9:
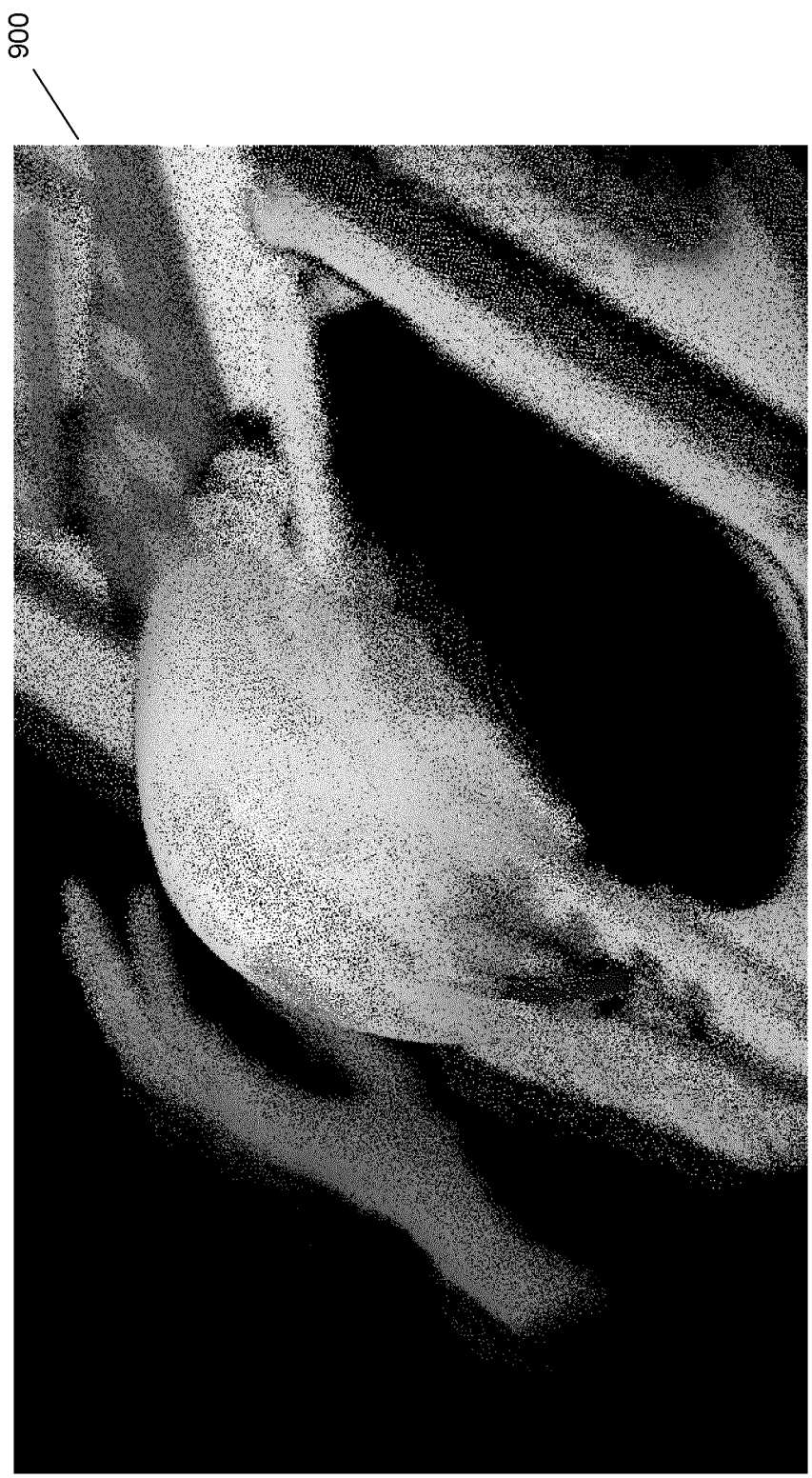
FIG. 9 is another screen shot illustrating occlusion handling.

Referring to FIG. 8 and FIG. 9, two images 800 and 900 respectively are shown that provide examples of occlusion handling that may be performed by aspects of the system and method described herein. A white head phantom is imaged that is occluded by a hand and then the hand is removed. The hand was differentiated from the head during the scan and can be removed, for example in the method 500. FIG. 8 shows the scanned image from a direction approximately perpendicular to the scan direction. FIG. 9 shows the hand and head from a direction slightly offset from the scan direction. As shown in FIGS. 8 and 9, the head surface is not affected by occlusion by the hand since the hand may be identified by method 500 as not part of the head.

Figure 7:
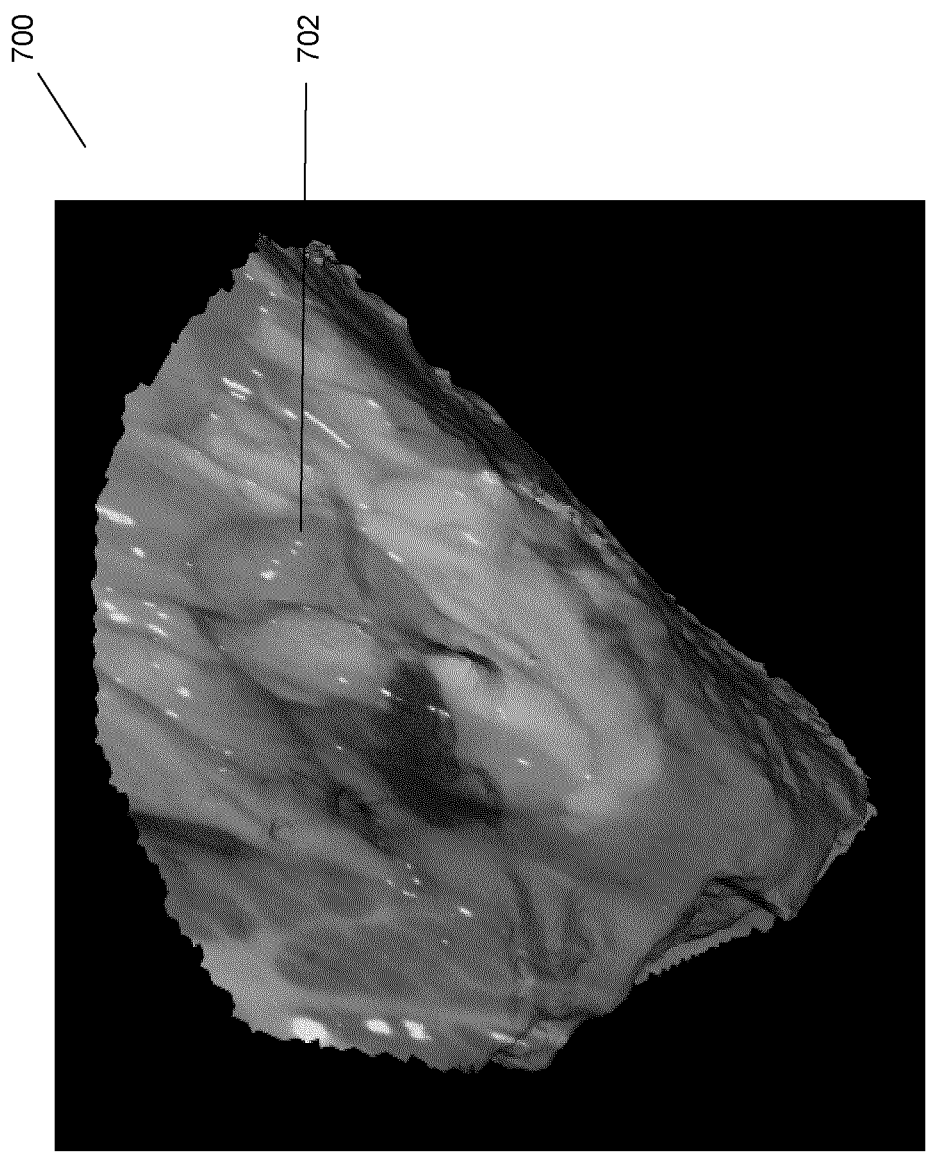
FIG. 7 is screen shot illustrating an exemplary frame of a 3D surface video.

Referring now to FIG. 7, is screen shot is shown illustrating an exemplary frame 700 of a 3D surface video 702, showing the target.

In one example, the block 512 may provide for augmenting the generated 3D surface video onto pre-operative images, which in one example may be 3 dimensional. In one example, displaying the 3D surface video on the display includes overlaying the 3D surface video onto a corresponding portion of pre-operative images displayed on the display. As the surgeon moves around the surgical site of interest and therefore shifts the focus of the video camera, the 3D surface video may also move such that the 3D surface video remains overlaid on the portion of the pre-operative images that corresponds to the 3D surface video, therefore guiding the surgeon to the appropriate surgical site of interest (e.g., a tumour to be removed).

Explained another way, in the present example the video captured from the video camera may be first projected on the 3D surface of the tissue and then snapped onto the 3D pre-op images of the patient (e.g., either MR or CT images). This visualization approach can be very useful as it allows surgeons to spatially correlate the real-time video feed with the pre-op images, providing high situational awareness, especially when the user starts interacting with the volume. This is similar to an augmented reality approach but instead of overlaying virtual data on real time video, the video is overlaid on the virtual data, commonly known as augmented virtuality.

In another example, the medical navigation system 205 further has a positioning device having a positioning arm (e.g., the robotic arm 305) with an end effector at the end of the positioning arm. The positioning device is electrically coupled to the controller, such as control and processing unit 300, and at least one of the 3D imaging device 309 and the video camera 307 is mountable on the end effector. With this configuration, the 3D scanning and video stream acquisition may be automatic and not need human direction.

The method 500 may be implemented in a medical navigation system, such as the medical navigation system 205 having control and processing unit 300. The medical navigation system 205 includes a 3D imaging device, such as 3D scanner 309, a video camera, such as video camera 307, a display, such as display 311, and a controller electrically coupled to the 3D imaging device, the video camera, and the display. The controller has a processor (e.g., processor 302) coupled to a memory (e.g., memory 304). The controller is configured to perform one or more of the blocks 502, 504, 506, 508, 510, and 512 of the method 500.

The specific embodiments described above have been shown by way of example, and it should be understood that these embodiments may be susceptible to various modifications and alternative forms. It should be further understood that the claims are not intended to be limited to the particular forms disclosed, but rather to cover modifications, equivalents, and alternatives falling within the spirit and scope of this disclosure.

We claim:

1. A medical navigation system for displaying a three dimensional (3D) surface video of a target, the medical navigation system comprising:
    a structured light 3D scanner;
    a camera;
    a display; and
    a controller electrically coupled to the 3D scanner, the camera, and the display, the controller having a processor coupled to a memory, the controller being configured to:
    acquire the 3D depth data of the target from a signal generated by the 3D scanner;
    construct a 3D surface contour, including a 3D point cloud, of the target based on the 3D depth data;
    acquire a video stream of the target from a signal generated by the camera;
    generate a 3D surface video based on the 3D surface contour and the video stream; and
    display the 3D surface video on the display;
    wherein the 3D surface contour is used by the controller to exclude occlusion events such that an object passing between the target and at least one of the 3D scanner and the camera is not visible in the 3D surface video.

2. The medical navigation system according to claim 1, further comprising:
    a positioning device having a positioning arm with an end effector at the end of the positioning arm, the positioning device electrically coupled to the controller and at least one of the 3D scanner and the camera being mountable on the end effector.

3. The medical navigation system according to claim 1, wherein the camera is selected from a group consisting of a video camera, an infrared camera, a visible light camera, and a non-visible light camera.

4. The medical navigation system according to claim 1, wherein the 3D surface video displayed on the display shows a 3D video that is dynamically rotatable about any axis.

5. The medical navigation system according to claim 1, wherein the display includes a two dimensional video display.

6. The medical navigation system according to claim 1, wherein the display includes a stereo display system.

7. The medical navigation system according to claim 1, wherein generating the 3D surface video includes coloring each point of the 3D point cloud using colour provided by the video stream.

8. The medical navigation system according to claim 1, wherein any objects having a depth that is beyond a threshold depth distance outside of the 3D surface contour are not shown in the 3D surface video.

9. The medical navigation system according to claim 1, wherein the target includes human tissue.

10. The medical navigation system according to claim 1, further comprising input devices including at least one of the 3D scanner, the camera, and a tracking system of the medical navigation system, the controller being further configured to:
    perform calibration of input devices by mapping coordinates of the input devices into a common coordinate system.

11. The medical navigation system according to claim 1, wherein displaying the 3D surface video on the display includes overlaying the 3D surface video onto a corresponding portion of pre-operative images displayed on the display.

12. A method for displaying a three dimensional (3D) surface video of a target in a system having a structured light 3D scanner, a camera, a display, and a controller electrically coupled to the 3D scanner, the camera, and the display, the method comprising:
    acquiring the 3D depth data of the target from a signal generated by the 3D scanner;
    constructing a 3D surface contour, including a 3D point cloud, of the target based on the 3D depth data;
    acquiring a video stream of the target from a signal generated by the camera;
    generating a 3D surface video based on the 3D surface contour and the video stream;
    displaying the 3D surface video on the display; and
    excluding occlusion events using the 3D surface contour such that an object passing between the target and at least one of the 3D scanner and the camera is not visible in the 3D surface video.

13. The method according to claim 12, wherein the system further has a positioning device having a positioning arm with an end effector at the end of the positioning arm, the positioning device electrically coupled to the controller and at least one of the 3D scanner and the camera being mountable on the end effector.

14. The method according to claim 12, wherein the camera is selected from a group consisting of a video camera, an infrared camera, a visible light camera, and a non-visible light camera.

15. The method according to claim 12, wherein the 3D surface video displayed on the display shows a 3D video that is dynamically rotatable about any axis.

16. The method according to claim 12, wherein the display includes a two dimensional video display.

17. The method according to claim 12, wherein the display includes a stereo display system.

18. The method according to claim 12, wherein generating a 3D surface video includes coloring each point of the 3D point cloud using colour provided by the video stream.

19. The method according to claim 12, wherein any objects having a depth that is beyond a threshold depth distance outside of the 3D surface contour are not shown in the 3D surface video.

20. The method according to claim 12, wherein the target includes human tissue.

21. The method according to claim 12, the method further comprising performing calibration of input devices by mapping coordinates of the input devices into a common coordinate system, wherein the input devices include at least one of the 3D scanner, the camera, and a tracking system of the medical navigation system.

22. The method according to claim 12, wherein displaying the 3D surface video on the display includes overlaying the 3D surface video onto a corresponding portion of pre-operative images displayed on the display.

* * * * *